US008778912B2

(12) United States Patent
Freixedas et al.

(10) Patent No.: US 8,778,912 B2
(45) Date of Patent: Jul. 15, 2014

(54) COMPOSITION OF DIALYSIS LIQUID COMPRISING CRYSTALLISATION INHIBITOR SUBSTANCES

(75) Inventors: Félix Grases Freixedas, Palma de Mallorca (ES); Joan Perello Bestard, Palma de Mallorca (ES); Fernando Tur Espinosa, Palma de Mallorca (ES); Antonia Costa Bauza, Palma de Mallorca (ES); Rafael M. Prieto Almirall, Palma de Mallorca (ES); Isabel Gomila Muñiz, Palma de Mallorca (ES)

(73) Assignee: Universitat de les Illes Balears, Edif. Son, Lledo, Palma de Mallorca (ES)

( * ) Notice: Subject to any disclaimer, the term of this patent is extended or adjusted under 35 U.S.C. 154(b) by 228 days.

(21) Appl. No.: 13/057,167

(22) PCT Filed: May 14, 2009

(86) PCT No.: PCT/ES2009/070156
§ 371 (c)(1),
(2), (4) Date: Mar. 23, 2011

(87) PCT Pub. No.: WO2010/018278
PCT Pub. Date: Feb. 18, 2010

(65) Prior Publication Data
US 2011/0172194 A1  Jul. 14, 2011

(30) Foreign Application Priority Data

Aug. 6, 2008 (ES) .................................. 200802363

(51) Int. Cl.
*A61K 31/675* (2006.01)
*A61K 31/66* (2006.01)
*A61K 31/663* (2006.01)
(52) U.S. Cl.
CPC ............. *A61K 31/663* (2013.01); *A61K 31/675* (2013.01)
USPC ............................................ 514/89; 514/141
(58) Field of Classification Search
CPC ........................... A61K 31/663; A61K 31/675
USPC .................................................. 514/89, 141
See application file for complete search history.

(56) References Cited

U.S. PATENT DOCUMENTS

| 4,752,586 | A | * | 6/1988 | Ropars et al. ............. 435/283.1 |
| 2007/0148258 | A1 | * | 6/2007 | O'Neill et al. ................ 424/601 |
| 2007/0219115 | A1 | * | 9/2007 | Coleman et al. .................. 514/2 |

OTHER PUBLICATIONS

Ariyoshi T, Eishi K, Sakamoto I, Matsukuma S, Odate T. Effect of etidronic acid on arterial calcification in dialysis patients. Clin Drug Investig. 2006;26(4):215-22.*
Saeki T, Shen JB, Pappano AJ. Inositol-1,4,5-trisphosphate increases contractions but not L-type calcium current in guinea pig ventricular myocytes. Cardiovasc Res. Mar. 1999;41(3):620-8.*
Halvorson KG, Sevcik MA, Ghilardi JR, Sullivan LJ, Koewler NJ, Bauss F, Mantyh PW. Intravenous ibandronate rapidly reduces pain, neurochemical indices of central sensitization, tumor burden, and skeletal destruction in a mouse model of bone cancer. J Pain Symptom Manage. Sep. 2008;36(3):289-303. Epub Apr. 14, 2008.*
Rao PS, Liu XK, Das DK, Weinstein GS, Tyras DH. Protection of ischemic heart from reperfusion injury by myo-inositol hexaphosphate, a natural antioxidant. Ann Thorac Surg. Oct. 1991;52(4):908-12. (abstract only).*
Jeroen Van der Kaay et al., "Desalting Inositolpolyphosphates by Dialysis," Analytical Biochemistry 1995, 225, pp. 183-185.
Laurence Boucher, et al., "Internalization and Distribution of Inositol Hexakisphosphate in Red Blood Cells," Biotechnology and Applied Biochemistry, Aug. 1, 1996, vol. 24, No. Part 01, pp. 73-78.
F. Grases, et al., "Effects of Phytate and Pyrophosphate on Brushite and Hydroxyapatite Crystallization: Comparison With the Action of Other Polyphosphates," Urological Research, Apr. 2000, vol. 28, No. 2, pp. 136-140.
Félix Grases, et al., "Phytate Inhibits Bovine Pericardium Calcification in Vitro," Cardiovascular Pathology, May 1, 2008, vol. 17, No. 3, pp. 139-145.

* cited by examiner

*Primary Examiner* — Paul Zarek
(74) *Attorney, Agent, or Firm* — Sterne, Kessler, Goldstein & Fox P.L.L.C.

(57) ABSTRACT

This invention relates to a composition that comprises inositol phosphates and/or bisphosphonates, and to the use thereof to prevent the loss of substances of biological interest in the body of patients subjected to dialysis and to maintain sufficient physiological levels of said substances to regulate physiological and/or pathological processes, these substances being inhibitors of pathological crystallization.

20 Claims, 2 Drawing Sheets

COMPOSITION OF DIALYSIS LIQUID COMPRISING CRYSTALLISATION INHIBITOR SUBSTANCES

CROSS-REFERENCE TO RELATED APPLICATIONS

The present application is a 35 U.S.C. §§371 national phase conversion of PCT/ES2009/070156, filed May 14, 2009, which claims priority of Spanish Patent Application No. P200802363, filed Aug. 6, 2008, the contents of which are incorporated herein by reference. The PCT International Application was published in the Spanish language.

This invention relates to a composition that comprises inositol phosphates and/or bisphosphonates, and to the use thereof to prevent the loss of substances of biological interest in the body of patients subjected to dialysis and maintain sufficient physiological levels of said substances to regulate physiological and/or pathological processes, these substances being inhibitors of pathological crystallisation.

PRIOR STATE OF THE ART

Acute renal dysfunction consists of a rapid decrease in the excretory renal function. Patients who suffer from this condition are treated with different therapeutic alternatives, which include haemodialysis and peritoneal dialysis.

Due to the lack of excretory function in renal failure processes, there is an accumulation of metabolic waste products. When the kidneys are incapable of performing their function, patients need to be subjected to dialysis processes or kidney transplantation in order to survive.

Dialysis is one of the alternatives used as a treatment for this alteration and involves the use of a semi-permeable membrane that separates the blood from another liquid called dialysing liquid or dialysis liquid.

In haemodialysis, an artificial kidney, the most important part whereof is the dialyser, is used. The latter is composed of a compartment for the blood and another compartment for the dialysis liquid, both fluids always circulating in opposite directions in order to make the maximum utilisation of diffusion in favour of the solute concentration gradient. Both compartments are separated by a semi-permeable membrane that, basically, may be of 4 different types:

Cellulose membrane (Cuprofan): it is the most widely used. It is composed of chains of glucose rings with numerous free hydroxyl groups.

Substituted cellulose membranes: they are obtained by means of a chemical bond between a large number of free hydroxyl radicals and acetate. Also called cellulose acetate.

Cellulosynthetic membranes: modification by the addition of a synthetic material, such as diethylaminoethyl in the production of Hemophan.

Synthetic membranes: they do not contain cellulose and are more permeable and more biocompatible than cellulose membranes. The varieties of this type of membranes include polyacrylonitrile, polysulfone, polyamide or polymethylmethacrylate.

In peritoneal dialysis, the operating scheme is analogous to that of haemodialysis, although the semi-permeable membrane used is the peritoneal mesothelium that coats the inner surface of the abdominal cavity and the organs inside it. Thus, the dialysis liquid is introduced into the peritoneal cavity, whereas the compartment for the blood is the lumen of the capillaries that irrigate the peritoneal mesothelium.

The composition of the dialysis liquid is such that, by means of a diffusion process, it makes it possible to eliminate waste substances from the blood and, additionally, makes it possible to regulate the volume of water and the electrolytic concentration thereof, due to its controlled composition of ions, such as, for example, sodium, potassium, chloride, magnesium or calcium.

This liquid also has a high glucose concentration (which makes it possible for it to achieve an isotonic osmolality with that of plasma) and is buffered with an acetate or bicarbonate buffer.

However, blood has naturally existing substances that are not present in the dialysis liquid, but which, nonetheless, are of biological interest. These substances undergo a clearance process when a dialysis process is performed using a semi-permeable membrane (Van der Kaay J., Van Haastert P. J. M., *Analytical Biochemistry* 1999; 225: 183-185). Moreover, this clearance process may eliminate up to 100% of the substance, a percentage that may be modified as a function of the medium's ionic strength.

DESCRIPTION OF THE INVENTION

There is a need to maintain effective physiological concentrations of certain substances that may contribute to regulate physiological and/or pathological crystallisation and calcification processes.

Specifically, it is necessary to improve the composition of dialysis liquids in order that, following the dialysis process whereto those patients needing it are subjected, the concentration of some biological substances in blood serum does not substantially decrease or to introduce certain substances in the dialysing liquid in order for the plasma concentration thereof following dialysis is adequate. Alternatively, given the modification of the concentration of said substances during the dialysis process, the plasma concentration thereof may be once again regulated by the administration of an intravenous formulation. The levels of said substances may be regulated by intravenous administration before, during or after the dialysis process whereto the patients are subjected.

Therefore, this invention relates to the introduction of substances of biological interest, for example, in dialysis liquid compositions and/or intravenous formulations and to the use thereof in order to prevent the loss of said substances from the blood, maintain adequate plasma levels or increase plasma levels to physiologically adequate values.

The interest of these substances and similar compounds for dialysed patients is particularly relevant if we take into consideration that renal failure leads to situations of hyperphosphataemia, which increases the oversaturation of calcium phosphate in the urine, and, therefore, may cause pathological cardiovascular calcification processes.

The objective of this invention is to introduce substances with an activity as crystallisation inhibitors in dialysis liquid compositions and/or intravenous formulations. Specifically, the purpose is to introduce inositol phosphates, more specifically phytate, and/or bisphosphonates into dialysis liquid compositions, and inositol phosphates, phytate amongst them, into intravenous formulations.

Specifically, this invention relates to dialysis liquid compositions and intravenous formulations that contain substances with an activity as crystallisation inhibitors. More particularly, these substances are inositol phosphates, preferably phytate, and/or bisphosphonates.

Bisphosphonates are synthetic compounds which are resistant to the enzymatic hydrolysis of phosphatases and, therefore, the exogenous supply thereof by oral route is more effective than that of pyrophosphate. Although the use thereof as drugs focuses on the treatment of bone resorption processes, they also have properties as inhibitors of the crystallisation of calcium salts. On the other hand, phytate, or myo-inositol hexaphosphate, is a molecule with outstanding properties as an inhibitor of the crystallisation of calcium salts, since it has 6 phosphate groups and, therefore, a high affinity for divalent ions such as calcium. Thus, preventive properties relative to the development of pathological calcifications, such as renal lithiasis or cardiovascular calcifications, have been described.

The introduction of substances into dialysis liquid compositions may prevent the loss thereof from the blood, maintain adequate plasma levels or increase the plasma levels thereof to physiologically adequate values. Alternatively, given the modification of the concentration of said substances during the dialysis process, the plasma concentration may once again be regulated by the administration of an intravenous formulation before, during or after the dialysis process.

In this invention, "crystallisation inhibitor" is understood to mean a substance that is capable of preventing, curbing or decreasing crystallisation in any of the stages thereof, whether nucleation, crystalline growth or aggregation.

In this invention, "dialysis liquid" or "dialysing liquid" is understood to mean an electrolytic solution similar to that of blood plasma which does not contain the waste substances that accumulate in the body in the case of renal failure. Said solution is used in dialysis processes in order to reduce the accumulation of metabolic waste products, regulate the plasma volume and regulate the concentration of electrolytes in the blood.

Those skilled in the art know that one of the key elements of the dialysis process is the dialysing membrane, which is a part of the artificial kidney, in the case of haemodialysis, and the peritoneal mesothelium, in the case of peritoneal dialysis. In both cases, the pore size of the membrane prevents the loss of macromolecules such as proteins during the dialysis process, but allows for the exchange of electrolytes and low-molecular-weight substances. Thus, suitable quantities of ions such as sodium, potassium, chloride, magnesium or calcium are introduced into the dialysis liquids used in order to maintain adequate plasma levels.

However, there are no descriptions of the incorporation of inositol phosphates and/or bisphosphonates into said dialysing liquid compositions, which would allow to prevent a reduction in the plasma concentration thereof during the dialysis process (due to the concentration gradient between the blood and the dialysing liquid that allows for diffusion and, therefore, the clearance of these substances) or maintain/increase the plasma concentration thereof following the dialysis process (FIGS. 1-4). In general, they are low-molecular-weight substances which, therefore, cross the pores of the semi-permeable membranes used in dialysis. Moreover, as an alternative to the method described above, the modification of the plasma concentration of inositol phosphates in patients may be corrected by the administration of an intravenous formulation.

These substances may be of natural origin, as in the case of phytate and other inositol phosphates, but synthetic substances that exert a similar function, as in the case of bisphosphonates, may also be introduced into the composition.

Therefore, a first aspect of this invention relates to a composition that comprises crystallisation inhibitory substances selected from the list that comprises inositol phosphate, bisphosphonate, the pharmaceutically acceptable salts or any of the combinations thereof, to be used in the preparation of a dialysis liquid.

Inositol phosphate may contain between 1 and 6 phosphate groups (inositol mono-, di-, tri-, tetra-, penta- and hexa-phosphate). In a preferred embodiment, the crystallisation inhibitory substance is inositol phosphate containing between 1 and 6 phosphate groups, more preferably, inositol hexaphosphate (also called phytic acid or phytate) and, even more preferably, myo-inositol hexaphosphate.

In a preferred embodiment, the crystallisation inhibitory substance is bisphosphonate, which is selected from the list that comprises etidronic acid, alendronic acid, risedronic acid, zoledronic acid, tiludronic acid, pamidronic acid, clodronic acid, ibandronic acid, the salts or any of the combinations thereof.

A preferred embodiment of the dialysis liquid or the intravenous formulation of the invention additionally comprises other compounds, such as, for example, without being limited thereto, pyrophosphate and/or any of the pharmaceutically acceptable salts thereof.

The concentration of these substances in the dialysis liquid and/or the intravenous formulation will be dependent on several factors, such as the composition of the dialysis liquid, the dialysis time, the severity of the renal dysfunction, etc. In this invention, stable dialysis liquid compositions have been made wherein the quantity of inositol phosphate and/or bisphosphonate ranges between 0.1 µM and 0.1 M. Preferably, the concentration of inositol phosphate and/or bisphosphonate ranges between 0.1 µM and 10 mM; more preferably, between 0.1 µM and 1 mM.

An example of a dialysis liquid composition (for both peritoneal dialysis and haemodialysis) whereto this type of substances could be added would be composed of glucose, sodium, potassium, chlorine, calcium, magnesium, buffer (primarily, without being limited thereto, bicarbonate or acetate), etc. On the other hand, the high glucose concentration makes it possible to regulate the osmolality such that it is isotonic with the plasma. In addition, dextrose, lactate, heparin, antibiotics or auxiliary compounds that perform a specific function may be introduced into the plasma.

Another aspect of this invention relates to a dialysis liquid that comprises crystallisation inhibitory substances selected from the list that comprises inositol phosphate, bisphosphonate, the pharmaceutically acceptable salts or any of the combinations thereof, and to the use thereof for both haemodialysis and peritoneal dialysis. This composition that contains a crystallisation inhibitory substance is used to maintain, increase or prevent a decrease in the plasma concentration of said inhibitory substance.

The composition of the invention may be incorporated into a dialysis liquid formulation or a formulation adapted for intravenous administration.

Therefore, another aspect of this invention relates to a composition that comprises inositol phosphate and/or any of the salts thereof in a form adapted for intravenous administration, to be used in the treatment or prevention of pathological processes associated with the de-regulation of the physiologically adequate levels of said substances in the blood plasma. The treatment or prevention of de-regularisation is performed by maintaining or increasing the levels of said substances in the patients' plasma.

The pathological processes associated with the de-regularisation of the physiologically adequate levels of said substances in the blood plasma are of a very diverse nature, and may refer, without being limited thereto, to any pathology associated with calcium disorders, such as, for example, renal lithiasis, cardiovascular calcification, calcinosis cutis, osteoporosis or calcium podagra. On the other hand, this disorder or de-regularisation is also related to oncology, specifically, some cancers, such as colon, bone or skin cancer.

In the case of the intravenous formulations, stable compositions have been prepared wherein the quantity of inositol phosphate to be administered ranges between 1 nmol/kg and 0.1 mol/kg (with respect to the weight of the subject receiving the formulation). Preferably, the concentration of inositol phosphate ranges between 0.01 µmol/kg and 10 mmol/kg; more preferably, between 0.1 µmol/kg and 1 mmol/kg.

The crystallisation inhibitory substance is preferably inositol phosphate containing between 1 and 6 phosphate groups, more preferably, inositol hexaphosphate and, even more preferably, myo-inositol hexaphosphate. Said composition may additionally comprise pyrophosphate.

An example of an intravenous formulation contains inositol phosphate, and could additionally contain sodium, chlorine, buffer and/or other excipients, vehicles and inhibitory substances such as bisphosphonates or pyrophosphate.

In this invention, "intravenous administration" is understood to include both injectable or direct administration, that is, the administration of the composition in the form of a bolus, whether alone or diluted, or intravenous infusion, where the composition is added through a venous channel, by intravenous drip.

On the other hand, another aspect of the invention relates to a combined preparation that comprises, at least, the composition of the invention and a dialysis liquid to be used separately, simultaneously or sequentially in the treatment or prevention of the regulation of the physiologically adequate levels of the inhibitory substances, maintaining or, increasing these levels, in the plasma of patients subjected to dialysis.

In a preferred embodiment, the composition of the invention used in the combined preparation is in a form adapted to intravenous administration.

Throughout the description and the claims, the word "comprises" and the variants thereof are not intended to exclude other technical characteristics, additives, components or steps. For those skilled in the art, other objects, advantages and characteristics of the invention will arise partly from the description and partly from the practise of the invention. The following examples and drawings are provided for illustrative purposes, and are not intended to limit the scope of this invention.

EXAMPLES

Below we will illustrate the invention by means of assays performed by the inventors, which show the specificity and effectiveness of the composition of the invention administered in the form of an injection, intravenous infusion or dialysis liquid.

Example 1

An artificial plasma (liquid with a composition similar to that of plasma) was prepared with 1.5 mM phytate, regulating the ionic strength with 0.15 M NaCl. 25 ml of this solution were dialysed for 20 hours against a 1-l volume of a 0.15 M NaCl solution without phytate (dialysing liquid model). The pH of both solutions was adjusted to 7.4 using bicarbonate buffer.

5-ml aliquots of the dialysing liquid were collected at times 0, 1, 3, 6 and 20 hours, and the quantity of phytate in each of them was determined. Moreover, the concentration of phytate in the artificial plasma was determined at times 0 and 20 hours.

Figure 1:
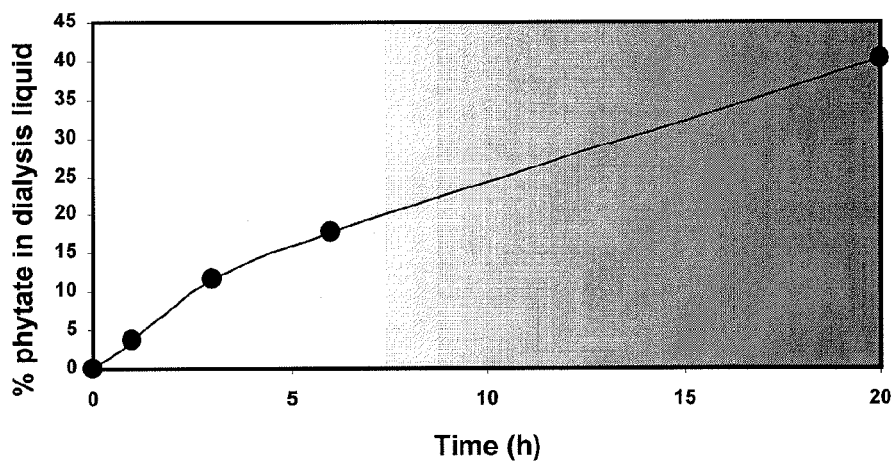
FIG. 1 shows that up to 40% of the phytate in an artificial blood plasma sample, during a dialysis process using a dialysis liquid without phytate, is lost by clearance in 20 hours.

The concentration of phytate in the artificial plasma after 20 hours of dialysis was 40% lower than the initial concentration. FIG. 1 shows that, during the dialysis process, clearance of the phytate takes place, increasing the quantity of phytate in the dialysis solution until 40% of the initial quantity in the artificial plasma is reached, after a 20-hour period.

Example 2

An artificial plasma was prepared with 1.5 mM of phytate, regulating the ionic strength with 0.15 M NaCl. 25 ml of this solution were dialysed for 20 hours against a 1-l volume of a 0.15 M NaCl solution with the same concentration of phytate as the plasma. The pH of both solutions was adjusted to 7.4 using bicarbonate buffer.

5-ml aliquots of the dialysing liquid were collected at times 0, 1, 3, 6 and 20 hours, and the quantity of phytate was determined in each of them. Moreover, the concentration of phytate in the artificial plasma was determined at times 0 and 20 hours.

During the dialysis process, there are no variations in the concentration of phytate, either in the plasma or the dialysing liquid; therefore, the introduction of phytate into the dialysing liquid prevents the loss of this substance in the blood.

Example 3

An artificial plasma was prepared with 300 µM of phytate, regulating the ionic strength with 0.15 M NaCl. 25 ml of this solution were dialysed for 20 hours against a 1-l volume of a 0.15 M NaCl solution with a concentration of phytate 5 times greater than that of the plasma. The pH of both solutions was adjusted to 7.4 using bicarbonate buffer.

5-ml aliquots of the dialysing liquid were collected at times 0, 1, 3, 6 and 20 hours, and the quantity of phytate was determined in each of them. Moreover, the concentration of phytate in the artificial plasma was determined at times 0 and 20 hours.

Figure 2:
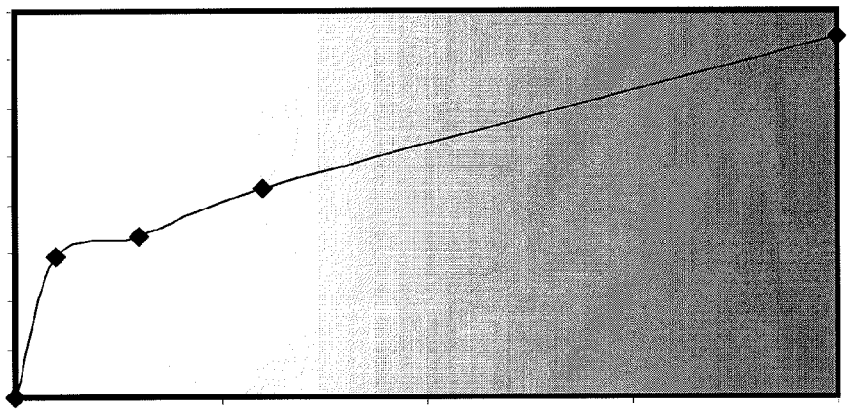
FIG. 2 shows that the phytate in an artificial blood plasma sample, during a dialysis process using a dialysis liquid with a phytate concentration greater than that of the plasma, makes it possible to increase the plasma concentration throughout a 20-hour period.

The results are shown in FIG. 2. It may be observed that, during the dialysis process, up to 0.75% of the phytate from the dialysis liquid enters into the artificial plasma; therefore, taking into consideration the ratio of initial volumes and concentrations, the concentration of phytate in the artificial plasma has increased by 140%; consequently, it is possible to re-establish normal values of phytate by introducing it into the dialysis liquid.

Example 4

An artificial plasma was prepared with 5 mM of etidronate, regulating the ionic strength with 0.15 M NaCl. 25 ml of this solution were dialysed for 20 hours against a 1-l volume of a 0.15 M NaCl solution without etidronate (dialysing liquid model). The pH of both solutions was adjusted to 7.4 using bicarbonate buffer.

5-ml aliquots of the dialysing liquid were collected at times 0, 1, 3, 6 and 20 hours, and the quantity of etidronate was determined in each of them. Moreover, the concentration of etidronate in the artificial plasma was determined at times 0 and 20 hours.

Figure 3:
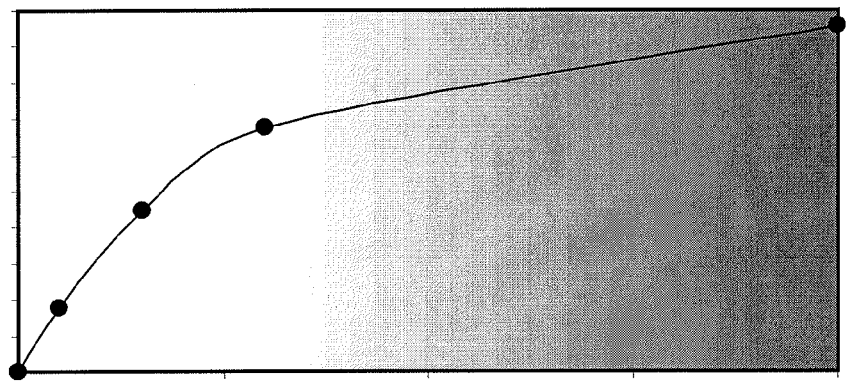
FIG. 3 shows that up to 95.6% of the etidronate in an artificial blood plasma sample, during a dialysis process using a dialysis liquid without etidronate, is lost by clearance in 20 hours.

The concentration of etidronate in the artificial plasma after 20 hours of dialysis was 95.6% lower than the initial concentration. In FIG. 3, it may be observed that, during the dialysis process, clearance of the etidronate takes place, increasing the quantity of etidronate in the dialysis solution to reach 95.6% of the initial quantity in the artificial plasma, after a 20-hour period.

Example 5

An artificial plasma was prepared with 5 mM of etidronate, regulating the ionic strength with 0.15 M NaCl. 25 ml of this solution were dialysed for 20 hours against a 1-l volume of a 0.15 M NaCl solution with the same concentration of etidronate as the plasma. The pH of both solutions was adjusted to 7.4 using bicarbonate buffer.

5-ml aliquots of the dialysing liquid were collected at times 0, 1, 3, 6 and 20 hours, and the quantity of etidronate was determined in each of them. Moreover, the concentration of etidronate in the artificial plasma was determined at times 0 and 20 hours.

During the dialysis process, there are no variations in the concentration of etidronate, either in the plasma or the dialysing liquid; therefore, the introduction of etidronate in the dialysing liquid prevents the loss of this substance in the blood.

Example 6

An artificial plasma was prepared with 1 mM of etidronate, regulating the ionic strength with 0.15 M NaCl. 25 ml of this solution were dialysed for 20 hours against a 1-l volume of a 0.15 M NaCl solution with a concentration of etidronate 5 times greater than that of the plasma. The pH of both solutions was adjusted to 7.4 using bicarbonate buffer.

5-ml aliquots of the dialysing liquid were collected at times 0, 1, 3, 6 and 20 hours, and the quantity of etidronate was determined in each of them. Moreover, the concentration of etidronate in the artificial plasma was determined at times 0 and 20 hours.

Figure 4:
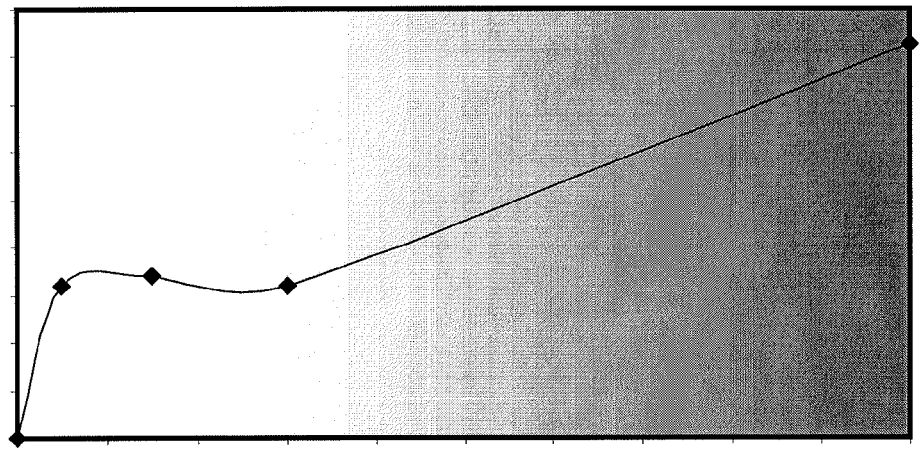
FIG. 4 shows that the etidronate in an artificial blood plasma sample, during a dialysis process using a dialysis liquid with a concentration of etidronate greater than that of the plasma, makes it possible to increase the plasma concentration throughout a 20-hour period.

The results are shown in FIG. 4. It may be observed that, during the dialysis process, up to 1.65% of the etidronate from the dialysis liquid enters into the artificial plasma; therefore, taking into consideration the ratio of initial volumes and concentrations, the concentration of etidronate in the artificial plasma has increased by 330%; consequently, it is possible to increase the plasma levels of etidronate by introducing it into the dialysis liquid.

Example 7

Dialysis liquid compositions (for both haemodialysis and peritoneal dialysis) whereto inositol phosphate and/or bisphosphonates are added:

| Compound | Composition 1 | Composition 2 |
|---|---|---|
| Inositol phosphate and/or bisphosphonate | 0.1 µM-0.1M | |
| glucose | 200 mg/dl | 250 mg/dl |
| sodium | 136 mEq/l | 146 mEq/l |
| potassium | 0 mEq/l | 3 mEq/l |
| chlorine | 96 mEq/l | 115 mEq/l |
| calcium | 2.5 mEq/l | 3.25 mEq/l |
| magnesium | 0.5 mEq/l | 1.5 mEq/l |
| buffer | 35 mEq/l | 40 mEq/l |

The high glucose concentration makes it possible to regulate the osmolality so that it is isotonic with the plasma. Moreover, dextrose, heparin, lactate, antibiotics and auxiliary compounds that perform a specific function may be introduced into the plasma.

Example 8

Compositions of formulations designed for intravenous administration in patients subjected to various medical procedures (both treatments by injection or intravenous infusion and haemodialysis or peritoneal dialysis), whereto inositol phosphates, including phytate, are added. The concentration of inositol phosphate is adjusted as a function of the volume of intravenous administration to obtain the quantities specified in the table.

| Compound | Composition 1 | Composition 2 |
|---|---|---|
| Inositol phosphate | 1 nmol/kg/day-0.1 mol/kg/day M | |
| sodium | — | 146 mEq/l |
| chlorine | — | 115 mEq/l |

Moreover, auxiliary compounds that perform a specific function may be introduced.

Example 9

6 male Wistar rats approximately 250 g in weight were acclimated from 7 dias in the animal house (T=1±1° C. and humidity=60±5%) with 12:12-hour light-darkness cycles. The rats were housed in Plexiglas cages, with one animal per cage, and fed with food and drink ad libitum.

Following the acclimation period, the animals were randomly divided into two groups with 3 rats each, a control group (with a diet without phytate, thereby simulating a post-dialysis physiological condition) and a treated group, which received 3 intravenous doses of 0.61 mmol/kg (400 mg/kg) separated by 12-hour periods. Following the last administration, 24-hour urine samples were collected in order to determine the phytate and, subsequently, the animals were anaesthesised and blood samples were collected.

The procedures used in this experiment were performed in accordance with Directive 86/609/EEC regarding the protection of animals used for experimental and scientific purposes.

The urinary excretions of phytate at the end of the study were statistically lower in the control group (4.0+/−1.5 □g) as compared to the treated group (72+/−10 µg). Upon comparing the plasma levels, a value of 0.013+/−0.006 mg/l was obtained for the control group and of 1.0+/−0.2 mg/l for the treated group; therefore, it was demonstrated for the first time that the administration of an intravenous formulation under conditions of plasma depletion of inositol phosphates is capable of correcting said deficient levels, achieving much higher plasma levels than may be achieved by means of oral administration, surprisingly even 24 hours after the intravenous administration thereof.

What is claimed is:

1. A dialysis liquid comprising a crystallisation inhibitory substance wherein:
   (i) the crystallization inhibitory substance is chosen from inositol phosphate, bisphosphonate, their pharmaceutically acceptable salts, and combinations thereof;
   (ii) the crystallisation inhibitory substance maintains, in the body of a subject undergoing dialysis, an effective physiological concentration of at least one substance that contributes to regulate at least one of physiological and pathological crystallization and calcification processes in said subject; and
   (iii) the composition has a dose of inositol phosphate and/or any of the pharmaceutically acceptable salts thereof between 1 nmol/kg and 0.1 mol/kg of body weight of the subject.

2. The dialysis liquid according to claim 1, wherein the crystallisation inhibitory substance is inositol phosphate containing between 1 and 6 phosphate groups.

3. The dialysis liquid according to claim 2, wherein the inositol phosphate is inositol hexaphosphate.

4. The dialysis liquid according claim 3, wherein the inositol phosphate is myo-inositol hexaphosphate.

5. The dialysis liquid according to claim 1, wherein the bisphosphonate is selected from among etidronic acid, alendronic acid, risedronic acid, zoledronic acid, tiludronic acid, pamidronic acid, clodronic acid, ibandronic acid, the salts thereof and combinations thereof.

6. The dialysis liquid according to claim 1, wherein said dialysis liquid comprises pyrophosphate.

7. The dialysis liquid according to claim 1, wherein the crystallisation inhibitory substance is present in said dialysis liquid in a concentration of between 0.01 µM and 0.1 M.

8. The dialysis liquid according to claim 7, wherein the crystallisation inhibitory substance is present in said dialysis liquid in a concentration of between 0.1 µM and 10 mM.

9. The dialysis liquid according to claim 8, wherein the crystallisation inhibitory substance is present in said dialysis liquid in a concentration of between 0.1 µM and 5 mM.

10. An intravenous composition that treats or prevents pathological processes associated with the de-regularisation of physiologically adequate levels of substances in the blood plasma of a subject, wherein the composition comprises at least one of inositol phosphate and any of its pharmaceutically acceptable salts, in a form adapted for intravenous administration; and wherein the composition has a dose, of inositol phosphate and/or any of the pharmaceutically acceptable salts thereof between 1 nmol/kg and 0.1 mol/kg of body weight of the subject.

11. The intravenous composition according to claim 10, wherein the inositol phosphate contains between 1 and 6 phosphate groups.

12. The intravenous composition according to claim 11, wherein the inositol phosphate is inositol hexaphosphate.

13. The intravenous composition according to claim 12, wherein the inositol phosphate is myo-inositol hexaphosphate.

14. The intravenous composition according to claim 10, which additionally comprises pyrophosphate.

15. The intravenous composition according to claim 10, wherein the treatment or prevention of the de-regularisation is performed by maintaining or increasing the levels of said substances in the plasma of a person subjected to dialysis.

16. A preparation that maintains, in the body of a subject undergoing dialysis, an effective physiological concentration of substances that contribute to regulate at least one of physiological and pathological crystallization and calcification processes in said subject, said preparation comprising,
   (i) a composition that comprises crystallisation inhibitory substances selected from among inositol phosphate, bisphosphonate, their pharmaceutically acceptable salts and any combinations thereof, and
   (ii) a dialysis liquid administered to said subject separately, simultaneously or sequentially from said composition to treat or prevent pathological processes associated with the de-regularisation of physiologically adequate levels of substances in the plasma of patients subjected to dialysis,
   wherein the composition has a dose of inositol phosphate and/or any of the pharmaceutically acceptable salts thereof between 1 nmol/kg and 0.1 mol/kg of body weight of the subject.

17. The preparation according to claim 16, wherein the preparation is in a form adapted for intravenous administration.

18. The dialysis liquid according to claim 1, wherein the subject suffers from decreased excretory renal function.

19. The intravenous composition according to claim 10, wherein the subject suffers from decreased excretory renal function.

20. The preparation according to claim 16, wherein the subject suffers from decreased excretory renal function.

* * * * *